(12) United States Patent
Konecky et al.

(10) Patent No.: US 11,259,706 B2
(45) Date of Patent: Mar. 1, 2022

(54) DUAL WAVELENGTH IMAGING AND OUT OF SAMPLE OPTICAL IMAGING

(71) Applicant: Open Water Internet Inc., San Francisco, CA (US)

(72) Inventors: Soren Konecky, Alameda, CA (US); Edgar Emilio Morales Delgado, San Francisco, CA (US); Albert P. Heberle, Santa Clara, CA (US)

(73) Assignee: Open Water Internet Inc., San Francisco, CA (US)

( * ) Notice: Subject to any disclaimer, the term of this patent is extended or adjusted under 35 U.S.C. 154(b) by 0 days.

(21) Appl. No.: 16/878,513

(22) Filed: May 19, 2020

(65) Prior Publication Data
US 2021/0364429 A1 Nov. 25, 2021

(51) Int. Cl.
| | |
|---|---|
| A61B 6/00 | (2006.01) |
| A61B 5/00 | (2006.01) |
| G01N 21/47 | (2006.01) |
| G01N 21/17 | (2006.01) |
| G01N 29/44 | (2006.01) |
| G01N 21/59 | (2006.01) |
| A61B 8/08 | (2006.01) |

(52) U.S. Cl.
CPC ............ *A61B 5/0097* (2013.01); *A61B 8/52* (2013.01); *G01N 21/1702* (2013.01); *G01N 21/47* (2013.01); *G01N 21/4788* (2013.01); *G01N 21/59* (2013.01); *G01N 29/44* (2013.01); *A61B 5/0073* (2013.01); *G01N 2021/1706* (2013.01); *G01N 2201/06113* (2013.01)

(58) Field of Classification Search
CPC combination set(s) only.
See application file for complete search history.

(56) References Cited

U.S. PATENT DOCUMENTS

| | | | |
|---|---|---|---|
| 3,573,362 | A | 4/1971 | Burchardt |
| 6,172,760 | B1 | 1/2001 | Son |
| 6,608,774 | B1 | 8/2003 | Rentzepis |
| 6,956,650 | B2 | 10/2005 | Boas |
| 7,119,906 | B2 | 10/2006 | Pepper |
| 7,460,248 | B2 | 12/2008 | Kurtz |
| 7,551,809 | B2 | 6/2009 | Taira |
| 7,610,082 | B2 | 10/2009 | Chance |
| 7,647,091 | B2 | 1/2010 | Ntziachristos |
| 7,728,986 | B2 | 6/2010 | Lasker |
| 7,804,070 | B1 | 9/2010 | Pan |
| 7,821,640 | B2 | 10/2010 | Koenig |
| 7,822,468 | B2 | 10/2010 | Stammes |
| 7,826,878 | B2 | 11/2010 | Alfano |

(Continued)

OTHER PUBLICATIONS

U.S. Appl. No. 16/878,502, Soren Konecky.
(Continued)

*Primary Examiner* — Joel F Brutus
(74) *Attorney, Agent, or Firm* — Freestone Intellectual Property Law PLLC; Aaron J. Visbeek

(57) ABSTRACT

A first signal is generated with a first light detector in response to an ultrasound signal encountering a first measurement beam. A second signal is generated with a second light detector in response to the ultrasound signal encountering a second measurement beam. The second measurement beam propagates through the sample and the first measurement beam propagates outside the sample.

17 Claims, 9 Drawing Sheets

(56) References Cited

U.S. PATENT DOCUMENTS

| | | |
|---|---|---|
| 7,898,649 B2 | 3/2011 | Masumura |
| 7,965,389 B2 | 6/2011 | Da Silva |
| 7,983,740 B2 | 7/2011 | Culver |
| 7,928,896 B2 | 8/2011 | Jin |
| 8,014,847 B2 | 9/2011 | Shastri |
| 8,120,784 B2 | 2/2012 | Da Silva |
| 8,170,651 B2 | 5/2012 | Lorenzo |
| 8,239,006 B2 | 8/2012 | Zhu |
| 8,263,947 B2 | 9/2012 | Da Silva |
| 8,289,502 B2 | 10/2012 | Yoshida |
| 8,326,567 B2 | 12/2012 | Masumura |
| 8,330,642 B2 | 12/2012 | Jin |
| 8,355,131 B2 | 1/2013 | Bakker |
| 8,357,915 B2 | 1/2013 | Guyon |
| 8,374,409 B2 | 2/2013 | Jochemsen |
| 8,416,421 B2 | 4/2013 | Wang |
| 8,450,674 B2 | 5/2013 | Yang |
| 8,451,450 B2 | 5/2013 | Heng |
| 8,520,921 B2 | 8/2013 | Ziegler |
| 8,525,998 B2 | 9/2013 | Yaqoob |
| 8,527,242 B2 | 9/2013 | Granot |
| 8,531,662 B2 | 9/2013 | Van Der Mark |
| 8,563,932 B2 | 10/2013 | Fang |
| 8,634,077 B2 | 1/2014 | Hu |
| 8,649,015 B2 | 2/2014 | Ichihara |
| 8,917,442 B2 | 3/2014 | Baym |
| 8,717,574 B2 | 5/2014 | Yang |
| 8,814,795 B2 | 8/2014 | Derode |
| 8,817,255 B2 | 8/2014 | Masumura |
| 8,830,573 B2 | 9/2014 | Cui |
| 8,847,175 B2 | 9/2014 | Laidevant |
| 8,937,284 B2 | 1/2015 | Fang |
| 8,954,130 B2 | 2/2015 | Masumura |
| 8,976,433 B2 | 3/2015 | Masumura |
| 9,012,869 B2 | 4/2015 | Andersson-Engels |
| 9,036,970 B2 | 5/2015 | Guyon |
| 9,037,216 B2 | 5/2015 | Hielscher |
| 9,057,695 B2 | 6/2015 | Masumura |
| 9,131,851 B2 | 9/2015 | Fukutani |
| 9,134,229 B2 | 9/2015 | Lesage |
| 9,179,842 B2 | 11/2015 | Nakaji |
| 9,207,171 B2 | 12/2015 | Nadakuditi |
| 9,234,841 B2 | 1/2016 | Wang |
| 9,282,932 B2 | 3/2016 | Kudo |
| 9,297,752 B2 | 3/2016 | Shimokawa |
| 9,304,490 B2 | 4/2016 | Masumura |
| 9,313,423 B2 | 4/2016 | Wang |
| 9,335,604 B2 | 5/2016 | Popovich |
| 9,335,605 B2 | 5/2016 | Wang |
| 9,341,569 B2 | 5/2016 | 'T Hooft |
| 9,354,166 B2 | 5/2016 | Judkewitz |
| 9,373,020 B2 | 6/2016 | Kudo |
| 9,407,796 B2 | 8/2016 | Dinten |
| 9,427,213 B2 | 8/2016 | Suzuki |
| 9,480,425 B2 | 11/2016 | Culver |
| 9,486,142 B2 | 11/2016 | Hielscher |
| 9,488,574 B2 | 11/2016 | Koehler |
| 9,509,956 B2 | 11/2016 | Piestun |
| 9,622,663 B2 | 4/2017 | Fang |
| 9,689,797 B2 | 6/2017 | Sun |
| 9,724,489 B2 | 8/2017 | Barbour |
| 9,730,649 B1 | 8/2017 | Jepsen |
| 9,750,413 B2 | 9/2017 | Sandusky |
| 10,420,469 B2 | 9/2019 | Sobek et al. |
| 2006/0122475 A1 | 6/2006 | Balberg et al. |
| 2010/0016732 A1 | 1/2010 | Wells |
| 2010/0094134 A1 | 4/2010 | Zhu et al. |
| 2011/0201914 A1 | 8/2011 | Wang et al. |
| 2012/0052947 A1 | 3/2012 | Yun |
| 2012/0070817 A1 | 3/2012 | Wang et al. |
| 2014/0009808 A1 | 1/2014 | Wang et al. |
| 2014/0081096 A1 | 3/2014 | Baym |
| 2014/0114181 A1 | 4/2014 | Wu |
| 2014/0303473 A1 | 10/2014 | Nanaumi |
| 2015/0182121 A1 | 7/2015 | Barbour |
| 2015/0238092 A1 | 8/2015 | Masumura |
| 2015/0241342 A1 | 8/2015 | Zhou |
| 2015/0346027 A1 | 12/2015 | Khare |
| 2015/0351635 A1 | 12/2015 | Cerussi |
| 2016/0085135 A1 | 3/2016 | Park |
| 2016/0157723 A1 | 6/2016 | Kanick |
| 2016/0216503 A1 | 7/2016 | Kim et al. |
| 2016/0262723 A1 | 9/2016 | Zhu |
| 2016/0363527 A1 | 12/2016 | Ruan |
| 2017/0118423 A1 | 4/2017 | Zhou |
| 2017/0163946 A1 | 6/2017 | Komanduri |
| 2017/0168565 A1 | 6/2017 | Cohen |
| 2017/0202633 A1 | 7/2017 | Liu |
| 2017/0230555 A1 | 8/2017 | Tabirian |
| 2017/0231501 A1 | 8/2017 | Culver |
| 2018/0070891 A1 | 3/2018 | Jepsen |
| 2019/0008388 A1 | 1/2019 | Ando et al. |
| 2019/0050618 A1 | 2/2019 | Khur-Yakub et al. |
| 2019/0072897 A1* | 3/2019 | Jepsen ................. G03H 1/0465 |
| 2019/0150745 A1 | 5/2019 | Sobek et al. |
| 2019/0306439 A1 | 10/2019 | Delgado et al. |
| 2019/0380587 A1 | 12/2019 | Newswanger |

OTHER PUBLICATIONS

Arridge et al. Nonuniqueness in diffusion-based optical tomography, Optics Letters, Jun. 1, 1998, vol. 23, No. 11, pp. 882-884.

Hofmann et al. Differential light detector, Rev. Sci. Instrum, Feb. 1979, vol. 50, No. 2, paes 249-252.

Freund et al. Memory Effects in Propagation of Ooptical Waves through Disordered Media, Physical Review Letters, Nov. 14, 1988, vol. 61, No. 20, pp. 2328-2331.

Goodman et al. Wavefront-Reconstruction Imaging Through Random Media, Jun. 15, 1966, vol. 8, No. 12, pp. 311-313.

Peng et al. Low loss liquid crystals for infrared applications, Liquid Crystal, 2014, vol. 41, No. 11, pp. 1545-1552.

International Searching Authority, Patent Cooperation Treaty, European Application No. PCT/US2021/24988, Notification Date: Jun. 29, 2021, 2 pages.

International Searching Authority, Patent Cooperation Treaty, Written Opinion of the International Searching Authority, European Application No. PCT/US2021/24988, dated Jun. 29, 2021, 8 pages.

International Searching Authority, Patent Cooperation Treaty, European Application No. PCT/US2021/24986, Notification Date: Jul. 7, 2021, 2 pages.

International Searching Authority, Patent Cooperation Treaty, Written Opinion of the International Searching Authority, European Application No. PCT/US2021/24986, dated Jul. 7, 2021, 8 pages.

Maneas, Efthymios, et al., Anatomically realistic ultrasound phantoms using gel wax with 3D printed mould, Physics in Medicine and Biology vol. 63, Issue 1, pp., 015033 (Date of Publication: Jan. 4, 2018).

* cited by examiner

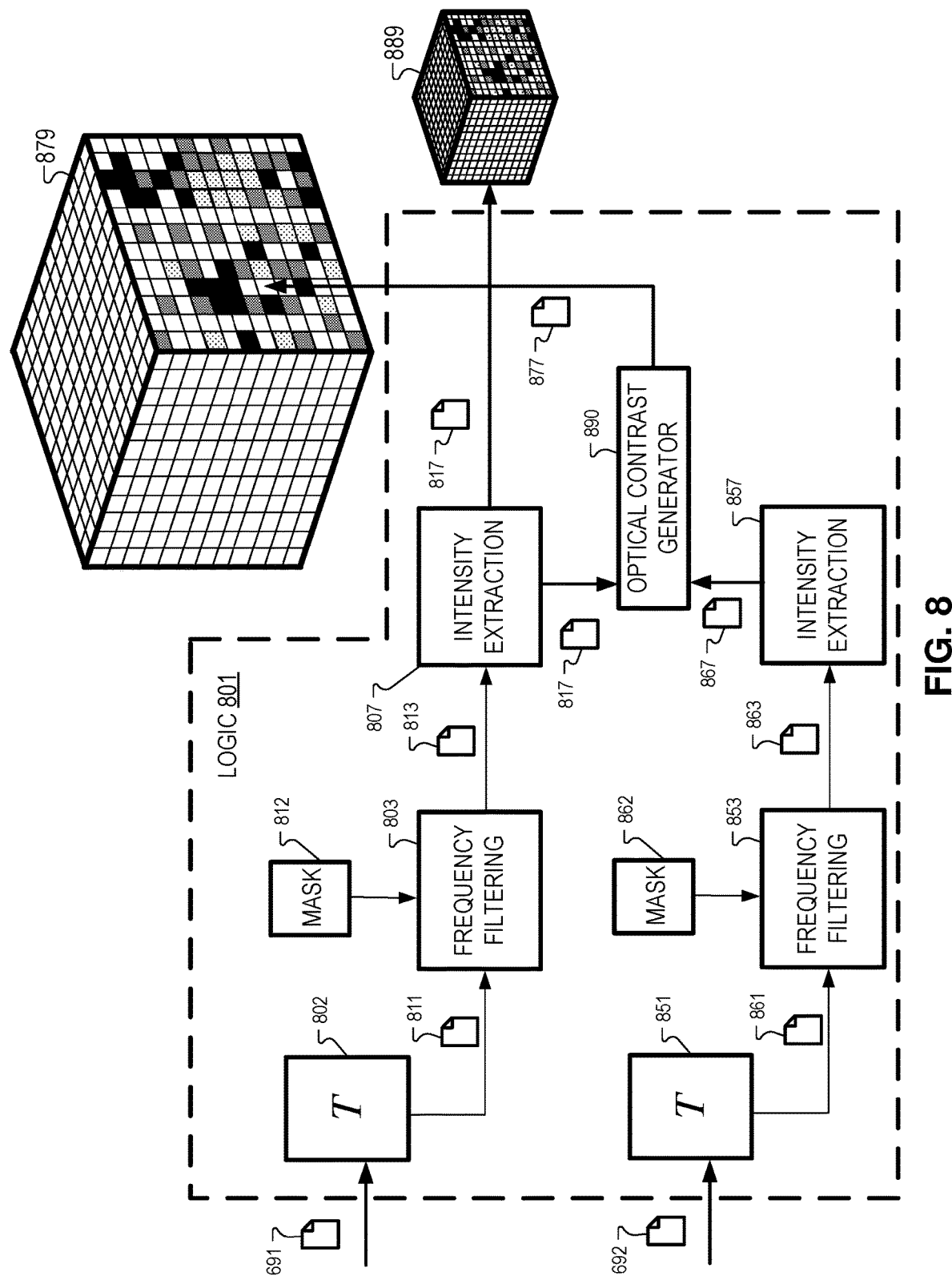

DUAL WAVELENGTH IMAGING AND OUT OF SAMPLE OPTICAL IMAGING

CROSS REFERENCE TO RELATED APPLICATIONS

This application is related to U.S. non-provisional patent application entitled, "Imaging with Scattering Layer" application Ser. No. 16/878,502 filed May 19, 2020, filed the same day.

BACKGROUND INFORMATION

Imaging devices are used in contexts such as healthcare, navigation, and security, among others. Imaging systems often measure radio waves or light waves to facilitate imaging. Imaging that measures light scattered by an object is especially challenging and advances to the devices, systems, and methods to improve optical imaging are sought to increase speed, increase resolution, reduce size and/or reduce cost.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

FIG. 8 illustrates processing logic for generating an optical contrast composite image of sample and/or a mechanical contrast composite image of sample, in accordance with aspects of the disclosure.

DETAILED DESCRIPTION

Figure 1:
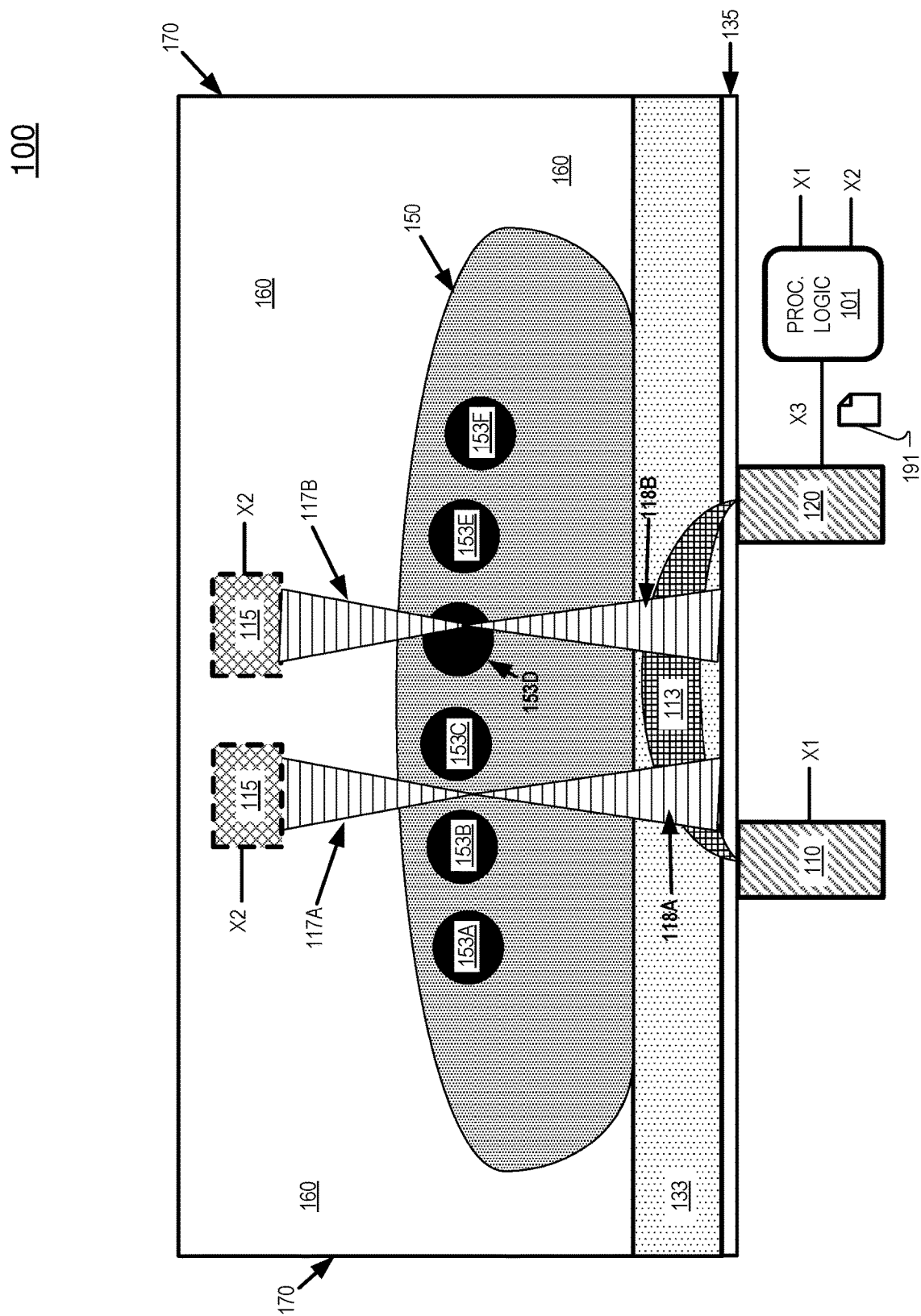
FIG. 1 illustrates an imaging system including a light source, a light detector, an ultrasound emitter, and a light scattering layer, in accordance with aspects of the disclosure.

Embodiments of out of sample imaging are described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In aspects of this disclosure, visible light may be defined as having a wavelength range of approximately 380 nm-700 nm. Non-visible light may be defined as light having wavelengths that are outside the visible light range, such as ultraviolet light and infrared light. Infrared light having a wavelength range of approximately 700 nm-1 mm includes near-infrared light. In aspects of this disclosure, near-infrared light may be defined as having a wavelength range of approximately 700 nm-1.4 µm.

In aspects of this disclosure, the term "transparent" may be defined as having greater than 90% transmission of light. In some aspects, the term "transparent" may be defined as a material having greater than 90% transmission of visible light.

This disclosure will generally describe imaging a diffuse medium in the context of human tissue in the medical context, however, the content of this disclosure may be applied to medical imaging, navigation, security, scientific research, or other contexts that image diffuse mediums or objects.

Human tissue is translucent to infrared light, although different parts of the human body (e.g. skin, blood, bone) exhibit different absorption and scattering coefficients. Researchers have attempted to use the properties of infrared light for medical imaging purposes, but size and cost constraints have been prohibitive for wide-scale adoption. Illuminating tissue and other diffuse media with near-infrared light for imaging purposes is sometimes referred to as Diffuse Optical Tomography. In one Diffuse Optical Tomography technique, time-of-flight (TOF) imaging can theoretically be employed by measuring the time it takes for "ballistic" photons (those photons that are not scattered) to pass through tissue. Since the ballistic photons reach the sensor the fastest, they are the least impeded (have the shortest optical path) and thus some conclusion can be drawn to create an image of the tissue that is illuminated by infrared light. However, TOF imaging generally requires specialty hardware (e.g. picosecond pulsed lasers and single photon detectors) to facilitate ultrafast shutters on sensors that are able to image at the speed of light and the systems are overall very expensive and bulky. TOF imaging also requires an input of approximately 10-100 fold (or more) light intensity into the body than is used at the detector; thus efficacy and power limitations as well as safety limits on input intensity limit TOF imaging resolution and utility.

In contrast to TOF imaging, some embodiments of this disclosure may include emitting laser light from a laser into a light scattering layer, emitting an ultrasound signal into a sample, and generating a signal with a light detector (e.g.

image pixel array) in response to a measurement beam of the laser light exiting the light scattering layer into the light detector. At least a portion of the measurement beam formed between the laser and the light detector is wavelength-shifted by the ultrasound signal subsequent to the ultrasound signal propagating through the sample. A first voxel value (corresponding to a voxel in the sample that the ultrasound is focused to) may be generated by the signal and the first voxel value may be incorporated into a composite image of the sample. Imaging techniques that include the scattering layer do not suffer from loss of interferometrical signal due to motion of the sample, which is especially useful when the sample is human tissue or animal tissue. The disclosed techniques are also amenable to use with continuous wave (CW) lasers rather than requiring high-power "pulsed lasers," (e.g. lasers delivering a high-intensity pulse with a pulse-width of approximately 250 ns or less) although the continuous wave laser light may be modulated or chopped, in some implementations. Furthermore, the disclosed techniques may offer higher sensitivity than conventional methods that measure ultrasound signals using an ultrasound receiver in an ultrasound transducer rather than measuring a laser light measurement beam.

In an implementation of the disclosure, a first signal is generated with a first light detector in response to an ultrasound signal encountering a first measurement beam and a second signal is generated with a second light detector in response to the ultrasound signal encountering a second measurement beam where the second measurement beam propagates through the sample and the first measurement beam propagates outside the sample. The first measurement beam may propagate through the scattering layer. A composite image of the sample may be generated based on the first signal and the second signal. In particular, a mechanical contrast value for a first voxel of the sample may be generated from the first signal and an optical contrast value for the first voxel may also be generated by reducing a representation of the second signal by the mechanical contrast value of the first voxel. As the ultrasound emitter raster-scans to different voxels and first and second signals are captured by the first and second light detectors for particular voxels, a two-dimensional or three-dimensional image of the sample can be generated.

In another implementation of the disclosure, laser light is emitted into an optically transmissive layer that is conducive to transmission of ultrasound frequencies and an ultrasound signal is emitted into the sample. The ultrasound signal exiting the sample may encounter the laser light propagating through the optically transmissive layer and diffract the laser light. A diffraction value of the laser light diffracted by the ultrasound signal is measured by a light detector such as a camera or a photodiode. The diffraction value may correspond to a mechanical contrast of a voxel of the sample that was focused on by the ultrasound signal. By iteratively scanning the ultrasound signal to different voxels, a composite image of the sample can be generated based on the diffraction values of laser light that is diffracted by the ultrasound signal exiting the sample. These embodiments and others will be described in more detail with reference to FIGS. 1-9D.

FIG. 1 illustrates an imaging system 100 including a light source 110, a light detector 120, an ultrasound emitter 115, and a light scattering layer 133, in accordance with aspects of the disclosure. Light source 110 may include a laser source and light detector 120 may include a camera having an image pixel array. Light source 110 may be a laser source configured to emit near-infrared laser light. In one embodiment, the near-infrared laser light has a wavelength between 700 nm and 1000 nm. Light source 110 may be a laser source configured to emit visible light. The visible light may be green light having a wavelength of approximately 550 nm. The laser may be a continuous wave (CW) laser. The output of the laser may be pulsed, chopped, or modulated. Imaging system 100 is able to image a sample 150. In the illustration of FIG. 1, sample 150 includes tissue that includes bones 153 (e.g. ribs).

Light source 110 is configured to emit light into scattering layer 133. In the illustration of FIG. 1, an optional transparent layer 135 (e.g. glass) is disposed between light source 110 and light scattering layer 133 and the optional transparent layer 135 is also disposed between light detector 120 and light scattering layer 133. Measurement beam 113 is the portion of the light emitted by light source 110 that exits into light detector 120. When light source 110 is a laser, measurement beam 113 includes laser light emitted by light source 110 into light scattering layer 133 that ultimately propagates to light detector 120. The light in measurement beam 113 may take a more round-about optical path than is illustrated in FIG. 1.

Scattering layer 133 is configured to scatter the light emitted by light source 110 and also configured to facilitate transmission of an ultrasound exit signal. In one embodiment, light scattering layer 133 includes gel wax that scatters light while also facilitating the transmission of an ultrasound signal. In an embodiment, the gel wax has a thickness between one centimeter and two centimeters.

Processing logic 101 is configured to control ultrasound emitter 115 by way of communication channel X2. Processing logic 101 is configured to selectively activate light source 110 by way of communication channel X1, although light source 110 may generally be left activated (ON) during imaging. Processing logic 101 is configured to control and/or synchronize the signal acquisition of light detector 120 with the emission of ultrasound signal 117 into sample 150. Processing logic 101 is configured to control light detector 120 and receive signal 191 by way of communication channel X3.

In operation, ultrasound emitter 115 emits an ultrasound signal 117 into sample 150. The ultrasound emitter 115 may be positioned more closely (or contacting) sample 150 in some implementations. An ultrasound transmitting fluid and/or lubricant 160 may be provided to facilitate the transmission of ultrasound signal 117 into sample 150. Ultrasound transmitting fluid 160 may be provided in a bath that the sample 150 is placed in and the ultrasound transmitting fluid 160 is contained by boundaries 170, in some implementations.

FIG. 1 illustrates that ultrasound emitter 115 may physically move to different positions in order to direct the ultrasound signal 117 to different coordinates of sample 150. For example, ultrasound signal 117A is emitted from a first position of ultrasound emitter 115 and ultrasound signal 117B is emitted from a second position of ultrasound emitter 115. Additionally, ultrasound emitter 115 may be a directional ultrasound emitter configured to direct the ultrasound signal to different coordinates in sample 150. Ultrasound emitter 115 may include an array of ultrasound transmitters that can direct the ultrasound signal 117 by way of beam-forming by coordinating operation of the ultrasound transmitters. Ultrasound emitter 115 may focus ultrasound signal 117 to different three-dimensional coordinates of sample 150.

Ultrasound signal 117A is emitted into sample 150 and propagates through sample 150 into scattering layer 133

(which is configured to facilitate ultrasound transmission) as ultrasound exit signal 118A. The ultrasound exit signal 118A that is exiting the sample 150 encounters measurement beam 113 as ultrasound exit signal 118 propagates through scattering layer 133. Measurement beam 113 is formed between light source 110 and light detector 120 and is positioned to receive the ultrasound exit signal 118A of the ultrasound signal exiting the sample 150. In some implementations, a plurality of light sources 110 and light detectors are utilized to provide a plurality of measurement beams 113 to measure the impact of the ultrasound exit signal 118. In other implementations, light source 110 and light detector 120 are spaced farther apart to extend the length of measurement beam 113.

Light detector 120 is configured to generate a signal 191 in response to measurement beam 113. Signal 191 may be an image and light detector 120 may include an image sensor to generate the image. Processing logic 101 is configured to receive signal 191 from light detector 120. Light detector 120 may include a CMOS (Complementary Metal-Oxide-Semiconductor) image sensor. In some embodiments, light detector 120 may include a charge-coupled device (CCD). In one embodiment, the image sensor has image pixels having a pixel pitch of one micron or less. The pixel resolution of the image sensor may vary depending on the application. In one embodiment, the image sensor is 1920 pixels by 1080 pixels. In one embodiment, the image sensor is 40 Megapixels or more.

Figure 2:
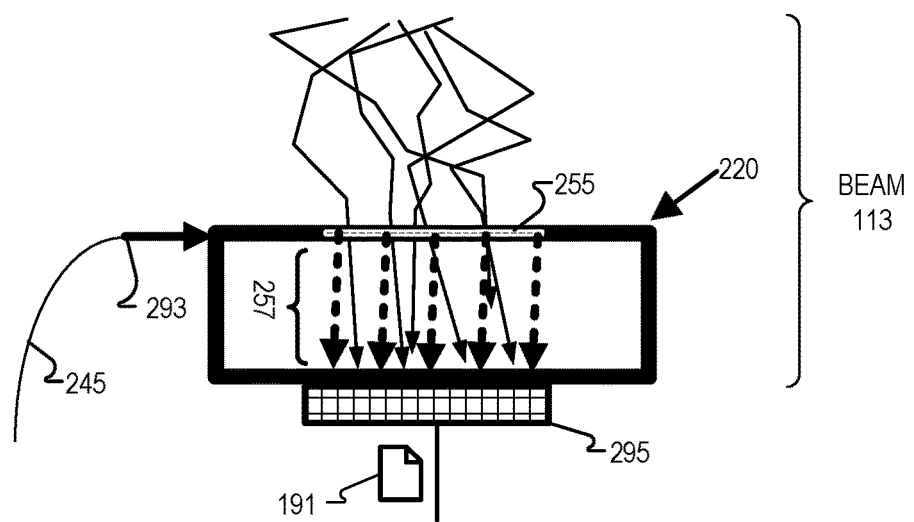
FIG. 2 illustrates an example light detector having an image sensor configured to image an interference pattern generated by a reference beam interfering with a measurement beam, in accordance with aspects of the disclosure.

FIG. 2 illustrates an example light detector 220 having an image sensor 295 configured to image an interference pattern generated by a reference beam 257 interfering with measurement beam 113, in accordance with aspects of the disclosure. Light detector 220 is configured to receive measurement beam 113. Reference beam 257 is the same wavelength as laser light emitted by a laser of light source 110, in some embodiments. Reference beam 257 may be provided to an optical input 293 of light detector 220 by a fiber optic 245 that receives laser light from a same source that generates the laser light to be emitted by light source 110 to ensure the wavelength of the reference beam 257 is the same as measurement beam 113. In the illustration of FIG. 2, a reference optical element 255 is configured to direct reference beam 257 to illuminate image sensor 295. Reference optical element 255 may include a surface relief grating, Bragg grating, and/or a holographic optical element coupled to receive the reference beam from optical input 293 and direct the reference beam 257 to image sensor 295. In some embodiments, the reference optical element 255 is configured to direct the reference beam 257 to become incident upon the image sensor 295 at an angle slightly offset from an angle that is perpendicular to an imaging plane of the image sensor 295.

Referring back to FIG. 1, ultrasound exit signal 118 wavelength-shifts a portion of measurement beam 113 so that a portion of measurement beam 113 no longer has the same wavelength of the laser light emitted by light source 110. When the ultrasound emitter 115 is focused to a voxel of sample 150 that has dense mechanical properties which reflect or absorb ultrasound, ultrasound exit signal 118A is significantly attenuated and will thus wavelength-shift a smaller portion of the measurement beam 113. And, when ultrasound emitter 115 is focused to a voxel of sample 150 that has sparse mechanical properties which do not reflect or absorb ultrasound (or reflect or absorb a small portion of an ultrasound signal), ultrasound exit signal 118A is attenuated to a lesser extent and will thus wavelength-shift a larger portion of the measurement beam 113 than when ultrasound signal 117 is focused to a dense voxel. In the context of FIG. 1, ultrasound signal 117B is focused to a denser voxel (e.g. bone in rib 153D) than ultrasound signal 117A. Thus, the lower-powered ultrasound exit signal 118B will wavelength-shift a lesser portion of measurement beam 113 so the interference pattern of measurement beam 113 and reference beam 257 will have a higher intensity. In other words, the greater the intensity of the interference of measurement beam 113 and reference beam 257, the greater density of the voxel of sample 150. Conversely, the higher-powered ultrasound exit signal 118A (encountering a less dense voxel than bone) will wavelength-shift a greater portion of measurement beam 113 so the interference pattern of measurement beam 113 and reference beam 257 will have less intensity. Thus, the intensity of the interference pattern captured in image 191 is representative of a mechanical property of the voxel that ultrasound emitter 115 was focusing ultrasound signal 117 to when the image 191 was captured.

Ultrasound emitter 115 can be raster-scanned and/or focused to different voxels corresponding to a plurality of images 191 to generate a two-dimensional or three-dimensional composite image of the sample 150 based on the images 191. In an embodiment, ultrasound emitter 115 is on mounted on a mechanical stage configured to raster scan through voxels of the sample and light detector 120 is configured to generate a corresponding signal 191 for each of the voxels of sample 150 in response to measuring the measurement beam 113 while the ultrasound emitter 115 is focused to a particular voxel.

Referring back to FIG. 2, light detector 220 is configured to capture an image 191 of the interference pattern generated by measurement beam 113 interfering with reference beam 257. Processing logic 101 may be configured to initiate the image capture by image sensor 295 via communication channel X3. The intensity of the interference pattern captured by the image sensor 295 of light detector 220 can be analyzed to determine how much light of measurement beam 113 was wavelength-shifted by the ultrasound exit signal 118 and thus the mechanical properties of the voxel that the ultrasound signal was focused to.

When the reference beam 257 is the same wavelength as the laser light emitted by light source 110, a brighter interference pattern in image 191 will indicate a higher density voxel and a dimmer interference pattern in image 191 will indicate a lower density voxel. However, in some embodiments, reference beam 257 may be configured to be the same wavelength as the wavelength-shifted light that ultrasound exit signal 118 wavelength-shifts from measurement beam 113 when ultrasound exit signal 118 encounters measurement beam 113. In those contexts, a stronger ultrasound exit signal 118 will wavelength-shift a greater portion of measurement beam 113 to generate a more intense interference of a wavelength-shifted reference beam 257 and the wavelength-shifted portion of measurement beam 113, and thus, a brighter interference pattern in image 191 will indicate a lower density voxel and a dimmer interference pattern in image 191 will indicate a higher density voxel.

Figure 3:
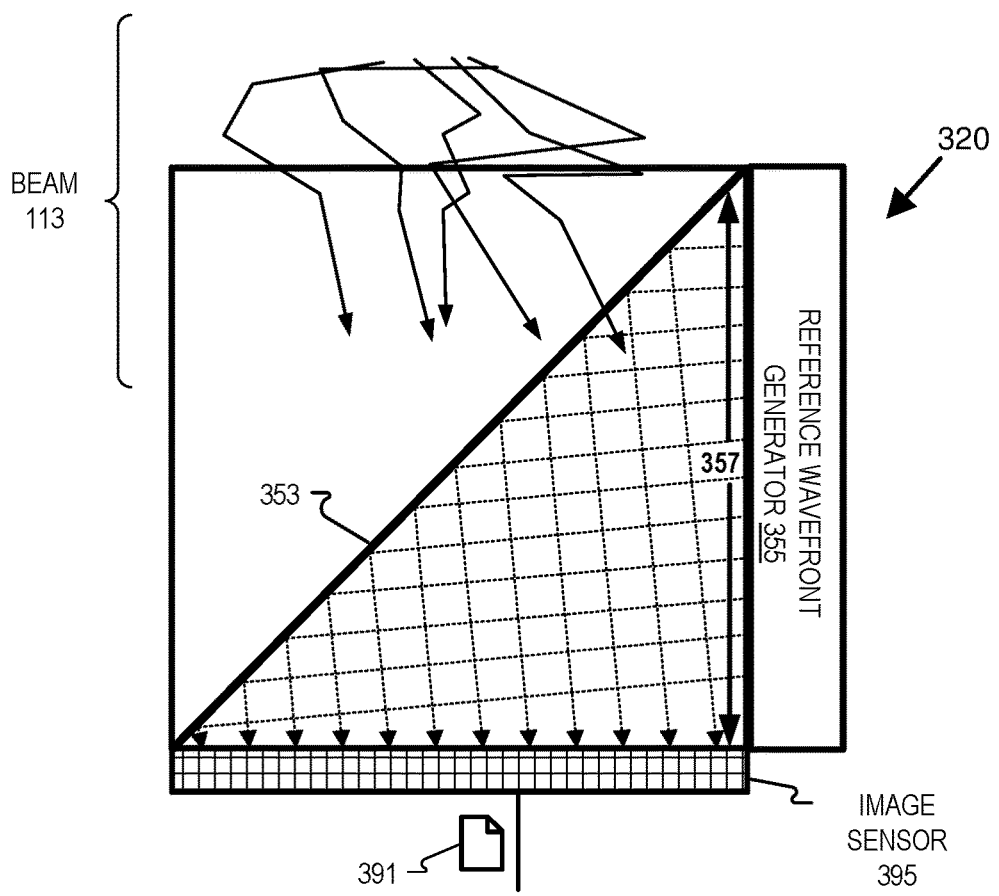
FIG. 3 illustrates an example configuration of a light detector including a beam splitter, in accordance with aspects of the disclosure.

FIG. 3 illustrates an additional example configuration of a light detector 320 that may be used as light detector 120, in accordance with aspects of the disclosure. Light detector 320 is configured to receive measurement beam 113. Light detector includes an image sensor 395 configured to capture an image 391 of an interference between the measurement beam and reference beam 357. At least a portion of measurement beam 113 propagates through beam splitter 353 to interfere with the portion of reference beam 357 that is reflected back toward image sensor 395. Therefore, image 391 generated by image sensor 395 is representative of an interference of the reference beam 357 with measurement beam 113.

Reference wavefront generator 355 generates a reference beam 357 that may be a near-infrared reference beam or a visible light reference beam. Reference wavefront generator 355 may include one or more lasers and corresponding optics to generate a substantially uniform wavefront for reference beam 357. Reference wavefront generator 355 may receive light from a same laser that provides laser light to light source 110, in some embodiments. Reference beam 357 may be the same wavelength as the laser light emitted from light source 110. Or, reference beam 357 may be the same wavelength as the wavelength-shifted portion of measurement beam 113, in some implementations.

In one embodiment, reference wavefront generator 355 is disposed to effect delivery of the reference beam 357 to image sensor 395 at an angle to a pixel plane of the image sensor 395. Image sensor 395 may include image pixels disposed in two-dimensional rows and columns that define the pixel plane of the image sensor 395. Processing logic 101 may be configured to initiate the image capture by image sensor 395 via communication channel X3.

Figure 4:
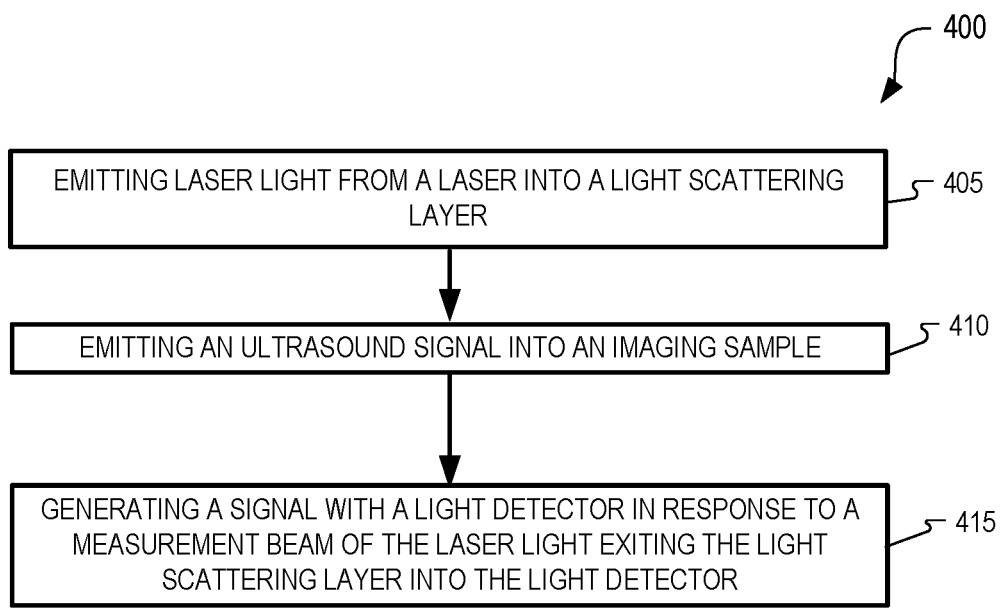
FIG. 4 illustrates an example flow chart of a process of imaging with a light scattering layer, in accordance with aspects of the disclosure.

FIG. 4 illustrates an example flow chart of a process 400 of imaging with a light scattering layer, in accordance with an embodiment of the disclosure. The order in which some or all of the process blocks appear in process 400 should not be deemed limiting. Rather, one of ordinary skill in the art having the benefit of the present disclosure will understand that some of the process blocks may be executed in a variety of orders not illustrated, or even in parallel. Processing logic 101 may execute some or all of the operations of process 400, for example.

In process block 405, laser light is emitted from a laser into a scattering layer (e.g. light scattering layer 133). Light source 110 may be a laser emitting laser light, for example. The laser light may be near-infrared laser light or visible laser light. The light scattering layer is configured to scatter the laser light. The light scattering layer may include gel wax.

In process block 410, an ultrasound signal (e.g. ultrasound signal 117) is emitted into a sample. The light scattering layer is configured to facilitate transmission of the ultrasound signal through the light scattering layer.

In process block 415, a signal (e.g. signal 191) is generated by a light detector (e.g. light detector 120) in response to a measurement beam (e.g. measurement beam 113) of the laser light exiting the light scattering layer into the light detector. At least a portion of the measurement beam formed between the laser and the light detector is wavelength-shifted by the ultrasound signal subsequent to the ultrasound signal propagating through the sample. The light detector may include an image sensor configured to capture an image of an interference between the measurement beam and a reference beam having a same wavelength as the measurement beam. When the measurement beam is near-infrared light, the reference beam is a near-infrared reference beam having a same wavelength as the measurement beam, for example.

Process 400 may further include emitting a second ultrasound signal into the sample and generating a second signal with the light detector in response to the measurement beam of the laser light exiting the light scattering layer into the light detector. The second ultrasound signal is focused to a second voxel of the sample. The ultrasound signal described in process block 410 is focused to a first voxel of the sample. Consequently, a first signal corresponding to the first voxel is generated by the light detector and a second signal corresponding to the second voxel is subsequently generated by the light detector. Of course, the ultrasound emitter may be iteratively focused on different voxels (e.g. a third voxel, a fourth voxel . . . and an nth voxel) as the ultrasound emitter raster-scans its focus through the sample to generate a two-dimensional (2D) or three-dimensional (3D) composite image of the sample where the light detector generates a signal corresponding to each voxel that the ultrasound signal is focused to. A first voxel value may be generated based on the signal generated in process block 415. A second voxel value may be generated based on the second signal and the first voxel value and the second voxel value may be incorporated into the composite image of the sample. Similarly, a third voxel value, a fourth voxel value . . . and an nth voxel value may be incorporated into a composite image of the sample.

In some implementations of process 400, a transparent layer (e.g. transparent layer 135) may be disposed between the light scattering layer and the laser. The transparent layer may be disposed between the light scattering layer and the light detector. The transparent layer may be a glass layer.

Figure 5:
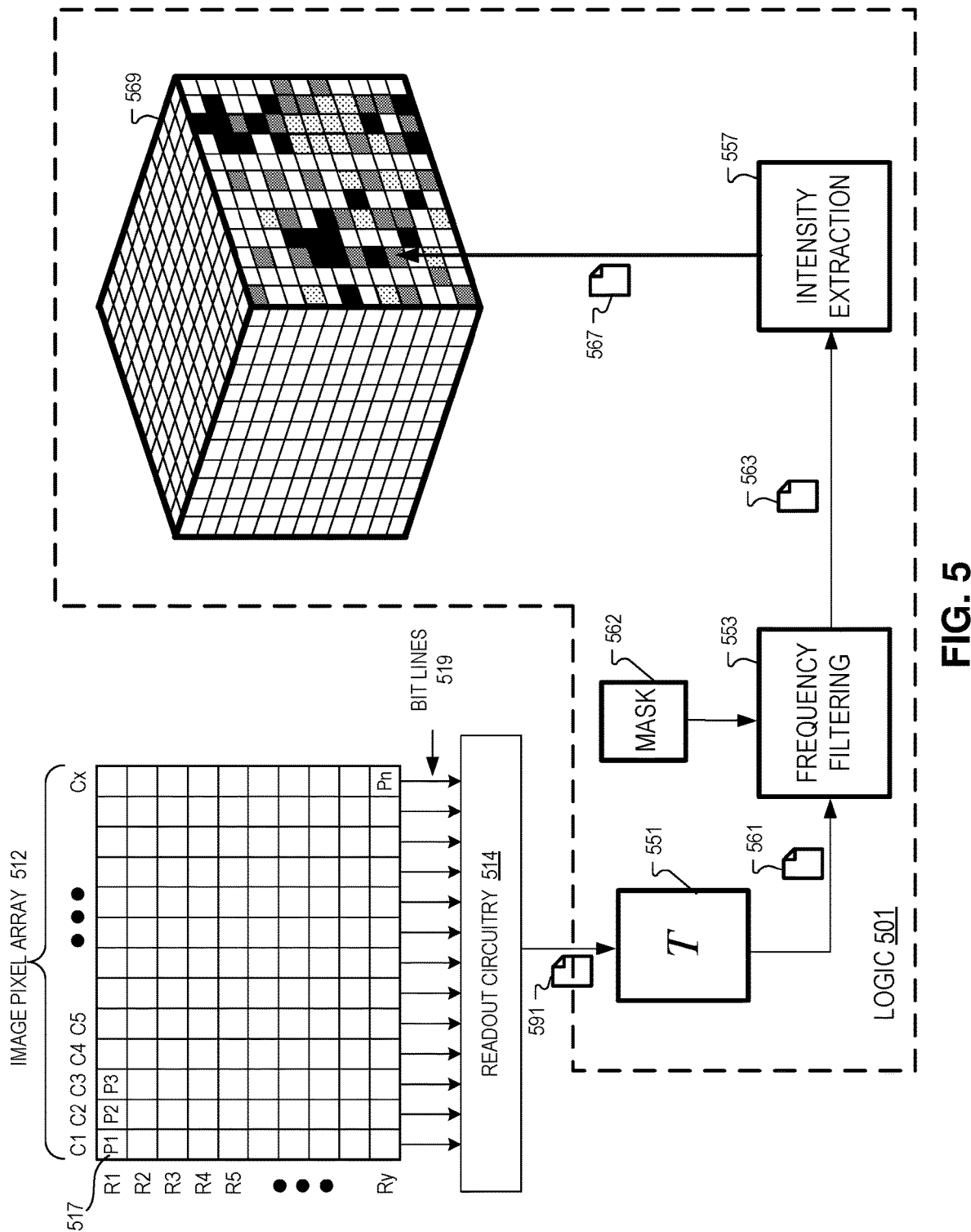
FIG. 5 illustrates an image pixel array coupled to processing logic configured to generate a composite image, in accordance with aspects of the disclosure.

FIG. 5 illustrates an image pixel array 512 coupled to example processing logic 501 that may be included in processing logic 101, in accordance with an embodiment of the disclosure. Image pixel array 512 may be included in a CMOS image sensor that is included in light detector 120, for example. Image pixel array 512 includes image pixels 517 arranged in integer number x columns and integer number y rows. Readout circuitry 514 is coupled to read the signal value from each image pixel 517 via bitlines 519. Transform engine 551 in processing logic 501 is coupled to receive the image 591 from readout circuitry 514, in FIG. 5. Image 591 may be an example of signal 191. Transform engine 551 generates a frequency domain image 561 by performing a Transform operation on image 591 received from readout circuitry 514. In one embodiment, the Transform operation includes an inverse Fourier transform. In one embodiment, the Transform operation includes a discrete cosine transform.

Frequency filtering engine 553 is coupled to receive the frequency domain image 561 from Transform engine 551 and also coupled to receive mask 562. Frequency filtering engine 553 is configured to multiply the frequency domain image 561 with the mask 562 to generate a filtered frequency domain image 563, in the illustrated embodiment of FIG. 5. Mask 562 is designed to isolate the frequency of the wavelength-shifted portion of measurement beam 113 for further processing. Mask 562 may include a matrix that includes '1' values for the portion of the frequency domain image 561 that corresponds to the wavelength-shifted portion of measurement beam 113 and '0' values for other wavelengths of the frequency domain image 561. In one embodiment, mask 562 is a two-dimensional Gaussian filter.

Intensity extraction engine 557 is coupled to receive the filtered frequency domain image 563 and configured to extract intensity data 567 from the filtered frequency domain image 563. In one embodiment, generating the intensity data 567 includes averaging intensity values of the filtered frequency domain image 563. In an embodiment where a Fourier transform is used as the transform operation in Transform engine 551, the Fourier coefficients are extracted from filtered frequency domain image 563 and a sum of the logarithm of the absolute value of the Fourier coefficients is calculated. The sum is then used as intensity data 567. In some implementations, intensity extraction engine 557 may compare the sum of the logarithm of the absolute value of the Fourier coefficients to a baseline interference pattern in a baseline image of measurement beam 113 incident on image pixel array 512 that is captured without a sample 150 present to generate intensity data 567 as a voxel value for a particular voxel that the ultrasound was focused to. In an embodiment, a baseline intensity value is subtracted from the sum of the logarithm of the absolute value of the Fourier coefficients of filtered frequency domain image 563 to generate intensity data 567 as a voxel value of composite image 569 for a particular voxel.

Processing logic 501 incorporates the intensity data 567 as a voxel value in a composite image 569. Composite image 569 is illustrated as a three-dimensional image in FIG. 5 and may be a three-dimensional image of a diffuse medium such as sample 150. As described in this disclosure, imaging system 100 may raster scan through sample 150 (focusing ultrasound emitter 115 to different voxels) to generate a 3D composite image of a diffuse medium or sample 150 by generating a plurality of signals 191 that correspond to the different voxels of the sample 150.

Figure 6:
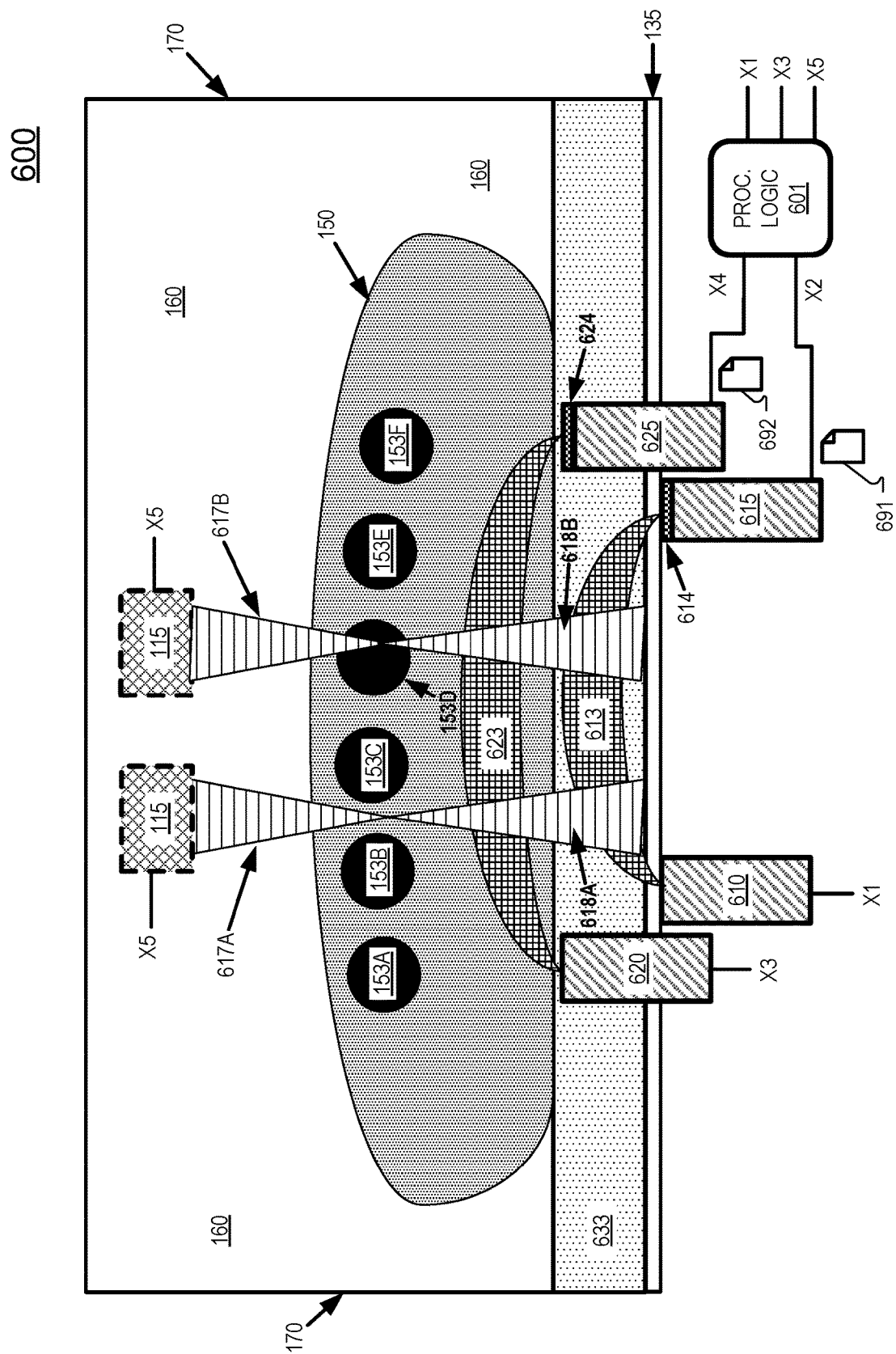
FIG. 6 illustrates an imaging system including a first light source, a second light source, a first light detector, a second light detector, an ultrasound emitter, and a light scattering layer, in accordance with aspects of the disclosure.

FIG. 6 illustrates an imaging system 600 including a first light source 610, a second light source 620, a first light detector 615, a second light detector 625, an ultrasound emitter 115, and a light scattering layer 633, in accordance with aspects of the disclosure. Light scattering layer 633 may be configured with similar features as light scattering layer 133.

First light source 610 may include a laser source and first light detector 615 may include a camera having an image pixel array. First light source 610 may be a laser source configured to emit visible light. In an embodiment, first light source 610 emits green light (e.g. wavelength approximately 550 nm). In an embodiment, first light source 610 emits light having a wavelength between 380 nm and 550 nm. In one embodiment, first light source 610 emits near-infrared laser light having a wavelength between 700 nm and 1000 nm. The laser may be a continuous wave (CW) laser. The output of the laser may be pulsed, chopped, or modulated.

First light source 610 is configured to emit light into scattering layer 633. The light emitted by first light source 610 may be confined to light scattering layer 633. In the illustration of FIG. 1, an optional transparent layer 135 (e.g. glass) is disposed between first light source 610 and light scattering layer 633 and the optional transparent layer 135 is also disposed between first light detector 615 and light scattering layer 633. Measurement beam 613 is the portion of the light emitted by first light source 610 that exits into first light detector 615. When first light source 610 is a laser, measurement beam 613 includes laser light emitted by first light source 610 into scattering layer 633 that ultimately propagates to first light detector 615. The light in measurement beam 613 may take a more round-about optical path due to scattering in light scattering layer 633 than is illustrated in FIG. 6.

Scattering layer 633 is configured to scatter the light emitted by light source 610 and also configured to facilitate transmission of an ultrasound exit signal. In one embodiment, light scattering layer 633 includes gel wax that scatters light while also facilitating the transmission of an ultrasound signal. In an embodiment, the gel wax has a thickness between one centimeter and two centimeters.

Second light source 620 may include a laser source and second light detector 625 may include a camera having an image pixel array. Second light source 620 may be a laser source configured to emit infrared light having a wavelength that propagates (at least to some extent) through tissue so that the infrared light penetrates into sample 150. In an embodiment, second light source 620 emits light having a wavelength between 700 nm and 800 nm. Of course, the light may have a very small linewidth (e.g. 3 nm or less) Second light source 620 emits light having a wavelength centered around 850 nm or 940 nm, in some examples. The laser may be a continuous wave (CW) laser. The output of the laser may be pulsed, chopped, or modulated.

Second light source 620 is configured to emit light into sample 150. An output aperture of second light source 620 may be positioned so that the second light source emits light into sample 150, but the light does not propagate through light scattering layer 633. In some embodiments, an output aperture of second light source 620 is positioned so that the light of measurement beam 623 only encounters a very thin layer of light scattering layer 633 so that the majority of the light propagates into sample 150. Measurement beam 623 is the portion of the light emitted by second light source 620 that propagates into sample 150 and exits sample 150 into second light detector 625. When second light source 620 is a laser, measurement beam 623 includes laser light emitted by second light source 620 into sample 150 that ultimately propagates to second light detector 625. The light in measurement beam 623 may take a more round-about optical path due to scattering in sample 150 than is illustrated in FIG. 6.

Light detector 625 may include a filter 624 that is configured to transmit the same wavelength of light emitted by second light source 620 and block other wavelengths. Light detector 615 may include a filter 614 that is configured to transmit the same wavelength of light emitted by first light source 610 and block other wavelengths. Light detectors 615 and/or 625 may be implemented with the designs of light detector 220 of FIG. 2 or the light detector 320 of FIG. 3.

Processing logic 601 is configured to control ultrasound emitter 115 by way of communication channel X5. Processing logic 601 is configured to selectively activate light source 610 by way of communication channel X1, although light source 610 may generally be left activated (ON) during imaging. Processing logic 601 is configured to selectively activate light source 620 by way of communication channel X3, although light source 620 may generally be left activated (ON) during imaging. Processing logic 601 is configured to control and/or synchronize the signal acquisition of light detector 615 and light detector 625 with the emission of ultrasound signal 617 into sample 150. Processing logic 601 is configured to control light detector 615 and receive signal 691 by way of communication channel X2. Processing logic 601 is configured to control light detector 625 and receive signal 692 by way of communication channel X4.

In operation, ultrasound emitter 115 emits an ultrasound signal 617 into sample 150. The ultrasound emitter 115 may be positioned more closely (or contacting) sample 150 in some implementations. An ultrasound transmitting fluid and/or lubricant 160 may be provided to facilitate the transmission of ultrasound signal 617 into sample 150. Ultrasound transmitting fluid 160 may be provided in a bath that the sample 150 is placed in and the ultrasound transmitting fluid 160 is contained by boundaries 170, in some implementations.

FIG. 6 illustrates that ultrasound emitter 115 may physically move to different positions in order to direct the ultrasound signal 617 to different coordinates of sample 150. For example, ultrasound signal 617A is emitted from a first position of ultrasound emitter 115 and ultrasound signal 617B is emitted from a second position of ultrasound emitter 115. Additionally, ultrasound emitter 115 may be a directional ultrasound emitter configured to direct the ultrasound signal to different coordinates in sample 150. Ultrasound emitter 115 may include an array of ultrasound transmitters that can direct the ultrasound signal 617 by way of beam forming by coordinating operation of the ultrasound transmitters. Ultrasound emitter 115 may focus ultrasound signal 617 to different three-dimensional coordinates of sample 150.

Ultrasound signal 617 is emitted into sample 150 and propagates through sample 150 into scattering layer 633 (which is configured to facilitate ultrasound transmission) as ultrasound exit signal 618. First measurement beam 613 and second measurement beam 623 are positioned to be encountered by the ultrasound signal. Ultrasound signal 617 encounters second measurement beam 623 within sample 150 and ultrasound signal 617 encounters first measurement beam 613 as an ultrasound exit signal 618 that is exiting the sample 150 as ultrasound exit signal 618 propagates through scattering layer 633.

First measurement beam 613 is formed between light source 610 and first light detector 615 and is positioned to receive the ultrasound exit signal 618 of the ultrasound signal exiting the sample 150. In some implementations, a plurality of light sources 610 and light detectors 615 are utilized to provide a plurality of measurement beams 613 to measure the impact of the ultrasound exit signal 618. In other implementations, light source 610 and light detector 615 are spaced farther apart to extend the length of measurement beam 613.

Second measurement beam 623 is formed between second light source 620 and second light detector 625 and is positioned to receive the ultrasound signal 617 propagating through sample 150. In some implementations, a plurality of light sources 620 and light detectors 625 are utilized to provide a plurality of measurement beams 623 to measure the impact of the ultrasound signal 617. In other implementations, light source 620 and light detector 625 are spaced farther apart to extend the length of measurement beam 623.

First light detector 615 is configured to generate a signal 691 in response to first measurement beam 613. Signal 691 may be an image and first light detector 615 may include an image sensor to generate the image. Processing logic 601 is configured to receive signal 691 from first light detector 615. First light detector 615 may include a CMOS (Complementary Metal-Oxide-Semiconductor) image sensor. In one embodiment, the image sensor has image pixels having a pixel pitch of one micron or less. The pixel resolution of the image sensor may vary depending on the application. In one embodiment, the image sensor is 1920 pixels by 1080 pixels. In one embodiment, the image sensor is 40 Megapixels or more. In some embodiments, first light detector 615 may include a charge-coupled device (CCD).

Second light detector 625 is configured to generate a signal 692 in response to second measurement beam 623. Second signal 692 may be generated by second light detector 625 during a same time period as the first signal 691. Signal 692 may be an image and second light detector 625 may include an image sensor to generate the image. Processing logic 601 is configured to receive signal 692 from second light detector 625. Second light detector 625 may include a CMOS (Complementary Metal-Oxide-Semiconductor) image sensor. In one embodiment, the image sensor has image pixels having a pixel pitch of one micron or less. The pixel resolution of the image sensor may vary depending on the application. In one embodiment, the image sensor is 1920 pixels by 1080 pixels. In one embodiment, the image sensor is 40 Megapixels or more. In some embodiments, second light detector 625 may include a charge-coupled device (CCD).

First signal 691 represents a mechanical contrast of a voxel of sample 150 that the ultrasound emitter 115 is focused to and second signal 692 represents both a mechanical contrast and an optical contrast of the voxel the ultrasound emitter 115 is focused to. Thus, first signal 691 provides mechanical contrast of the voxel and the optical contrast of the voxel can be determined by subtracting the mechanical contrast from second signal 692 (that represents mechanical contrast+optical contrast).

Figure 7:
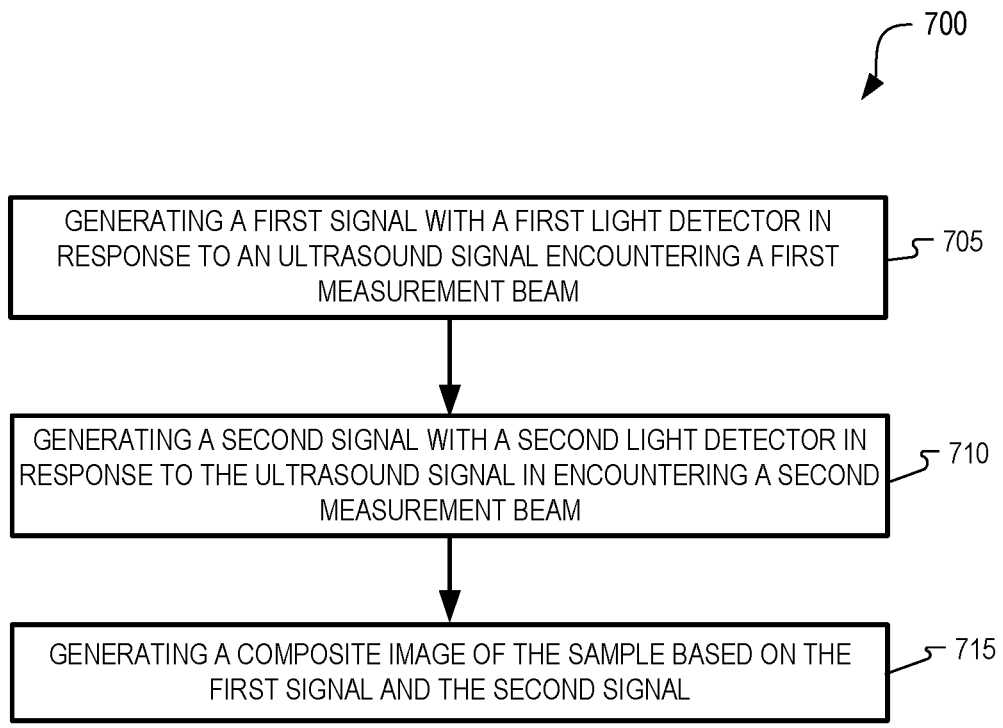
FIG. 7 illustrates an example flow chart of a process of imaging a sample, in accordance with aspects of the disclosure.

FIG. 7 illustrates an example flow chart of a process 700 of imaging a sample, in accordance with an embodiment of the disclosure. The order in which some or all of the process blocks appear in process 700 should not be deemed limiting. Rather, one of ordinary skill in the art having the benefit of the present disclosure will understand that some of the process blocks may be executed in a variety of orders not illustrated, or even in parallel. Processing logic 601 may execute some or all of the operations of process 700, for example.

In process block 705, a first signal (e.g. signal 691) is generated with a first light detector (e.g. first light detector 615) in response to an ultrasound signal encountering a first measurement beam (e.g. 613).

Generating the first signal may include emitting first laser light from a first laser where the first measurement beam is the first laser light propagating between the first laser and the first light detector. At least a portion of the first measurement beam formed between the first laser and the first light detector may be wavelength-shifted by the ultrasound signal subsequent to the ultrasound signal propagating through the sample.

The first laser light may be emitted into a light scattering layer configured to scatter the first laser light. The first light detector may be configured to receive the first measurement beam from the light scattering layer.

In process block 710, a second signal (e.g. signal 692) is generated with a second light detector (e.g. second light detector 625) in response to the ultrasound signal encountering a second measurement beam (e.g. 623). The second measurement beam propagates through the sample and the first measurement beam propagates outside the sample.

Generating the second signal may include emitting second laser light from a second laser having a second wavelength different from a first wavelength of the first laser light. The second measurement beam is the second laser light propagating between the second laser and second light detector. At least a portion of the second measurement beam formed between the second laser and the second light detector may be wavelength-shifted by the ultrasound signal propagating through the sample.

In process block 715, a composite image of the sample is generated based on the first signal and the second signal. Generating the composite image may include generating a mechanical contrast value from the first signal and generating an optical contrast value. Generating the optical contrast value may include reducing a representation of the second signal by the mechanical contrast value. The optical contrast value may be incorporated as a voxel value into the composite image of the sample if the composite image is an optical contrast composite image. The mechanical contrast value may be incorporated into a mechanical contrast composite image of the sample as a second voxel value.

To image a second voxel of the sample, process 700 may further include focusing a second ultrasound signal to a second voxel in the sample subsequent to the ultrasound signal being focused to a first voxel of the sample. A third signal is generated with the first light detector in response to the second ultrasound signal encountering the first measurement beam and a fourth signal is generated with the second light detector in response to the second ultrasound signal encountering the second measurement beam. The composite image of process block 715 may be augmented based on the third signal and the fourth signal.

The first measurement beam may have a first wavelength of less than 600 nm. The second measurement beam may have a second wavelength between 600 nm and 1000 nm.

FIG. 8 illustrates processing logic 801 that may be included in processing logic 601 for generating an optical contrast composite image 879 of sample 150 and/or a mechanical contrast composite image 889 of sample 150, in accordance with an embodiment of the disclosure. Transform engine 802 in processing logic 801 is coupled to receive image 691 from a camera of first light detector 615 and Transform engine 851 in processing logic 801 coupled to receive image 692 from a camera of second light detector 625.

Transform engine 802 generates a frequency domain image 811 by performing a Transform operation on image 691. In one embodiment, the Transform operation includes an inverse Fourier transform. In one embodiment, the Transform operation includes a discrete cosine transform. Frequency filtering engine 803 is coupled to receive the frequency domain image 811 from Transform engine 802 and also coupled to receive mask 812. Frequency filtering engine 803 is configured to multiply the frequency domain image 811 with the mask 812 to generate a filtered frequency domain image 813, in the illustrated embodiment of FIG. 8. Mask 812 is designed to isolate the frequency of the wavelength-shifted portion of measurement beam 613 for further processing. Mask 812 may include a matrix that includes '1' values for the portion of the frequency domain image 811 that corresponds to the wavelength-shifted portion of measurement beam 613 and '0' values for other wavelengths of the frequency domain image 811. In one embodiment, mask 812 is a two-dimensional Gaussian filter.

Intensity extraction engine 807 is coupled to receive the filtered frequency domain image 813 and configured to extract intensity data 817 from the filtered frequency domain image 813. In one embodiment, generating the intensity data 817 includes averaging intensity values of the filtered frequency domain image 813. In an embodiment where a Fourier transform is used as the transform operation in Transform engine 802, the Fourier coefficients are extracted from filtered frequency domain image 813 and a sum of the logarithm of the absolute value of the Fourier coefficients is calculated. The sum is then used as intensity data 817. In some implementations, intensity extraction engine 807 may compare the sum of the logarithm of the absolute value of the Fourier coefficients to a baseline interference pattern in a baseline image of measurement beam 613 incident on an image pixel array of first light detector 615 that is captured without a sample 150 present to generate intensity data 817 as a voxel value for a particular voxel that the ultrasound was focused to. In an embodiment, a baseline intensity value is subtracted from the sum of the logarithm of the absolute value of the Fourier coefficients of filtered frequency domain image 813 to generate intensity data 817. Intensity data 817 may be used as a voxel value of a mechanical contrast composite image 889 for a particular voxel, in some implementations.

Mechanical contrast composite image 889 is illustrated as a three-dimensional image in FIG. 8 and may be a three-dimensional image of sample 150. As described in this disclosure, imaging system 600 may raster scan through sample 150 (focusing ultrasound emitter 115 to different voxels) to generate a three-dimensional image of a diffuse medium such as sample 150. In FIG. 8, intensity data 817 is also provided to optical contrast generator engine 890 for generating an optical contrast value as a voxel value in an optical contrast composite image 879.

Transform engine 851 generates a frequency domain image 861 by performing a Transform operation on image 692. In one embodiment, the Transform operation includes an inverse Fourier transform. In one embodiment, the Transform operation includes a discrete cosine transform. Frequency filtering engine 853 is coupled to receive the frequency domain image 861 from Transform engine 851 and also coupled to receive mask 862. Frequency filtering engine 853 is configured to multiply the frequency domain image 861 with the mask 862 to generate a filtered frequency domain image 863, in the illustrated embodiment of FIG. 8. Mask 862 is designed to isolate the frequency of the wavelength-shifted portion of measurement beam 623 for further processing. Mask 862 may include a matrix that includes '1' values for the portion of the frequency domain image 861 that corresponds to the wavelength-shifted portion of measurement beam 623 and '0' values for other wavelengths of the frequency domain image 861. In one embodiment, mask 862 is a two-dimensional Gaussian filter.

Intensity extraction engine 857 is coupled to receive the filtered frequency domain image 863 and configured to extract intensity data 867 from the filtered frequency domain image 863. In one embodiment, generating the intensity data 867 includes averaging intensity values of the filtered frequency domain image 863. In an embodiment where a Fourier transform is used as the transform operation in Transform engine 851, the Fourier coefficients are extracted from filtered frequency domain image 863 and a sum of the logarithm of the absolute value of the Fourier coefficients is calculated. The sum is then used as intensity data 867. In some implementations, intensity extraction engine 857 may compare the sum of the logarithm of the absolute value of the Fourier coefficients to a baseline interference pattern in a baseline image of measurement beam 623 incident on an image pixel array of second light detector 625 that is captured without a sample 150 present to generate intensity data 867 as a voxel value for a particular voxel that the ultrasound was focused to. In an embodiment, a baseline intensity value is subtracted from the sum of the logarithm of the absolute value of the Fourier coefficients of filtered frequency domain image 863 to generate intensity data 867. Intensity data 867 is then provided to optical contrast generator engine 890.

Optical contrast generator engine 890 receives intensity data 817 of the interference pattern of measurement beam 613 upon an image sensor of first light detector 615 and optical contrast generator engine 890 also receives intensity data 867 of the interference pattern of measurement beam 623 upon an image sensor of second light detector 625. To generate an optical contrast value 877 as a voxel value for optical contrast composite image 879, optical contrast generator engine 890 may reduce the intensity data 867 (representing mechanical contrast and optical contrast of a voxel the ultrasound signal is focused to) by intensity data 817 (representing mechanical contrast of a voxel the ultrasound signal is focused to). A scale factor may be applied to intensity data 867 and/or intensity data 817 prior to the reduction to generate optical contrast value 877.

Processing logic 801 incorporates optical contrast value 877 as a voxel value in optical contrast composite image 879. Optical contrast composite image 879 is illustrated as a three-dimensional image in FIG. 8 and may be a three-dimensional image of a diffuse medium such as sample 150. As described in this disclosure, imaging system 600 may raster scan through sample 150 (focusing ultrasound emitter 115 to different voxels) to generate a three-dimensional image of a diffuse medium such as sample 150. Thus, imaging system 600 may generate an optical contrast composite image 879 and optionally generate a mechanical contrast composite image 889.

Figure 9A:
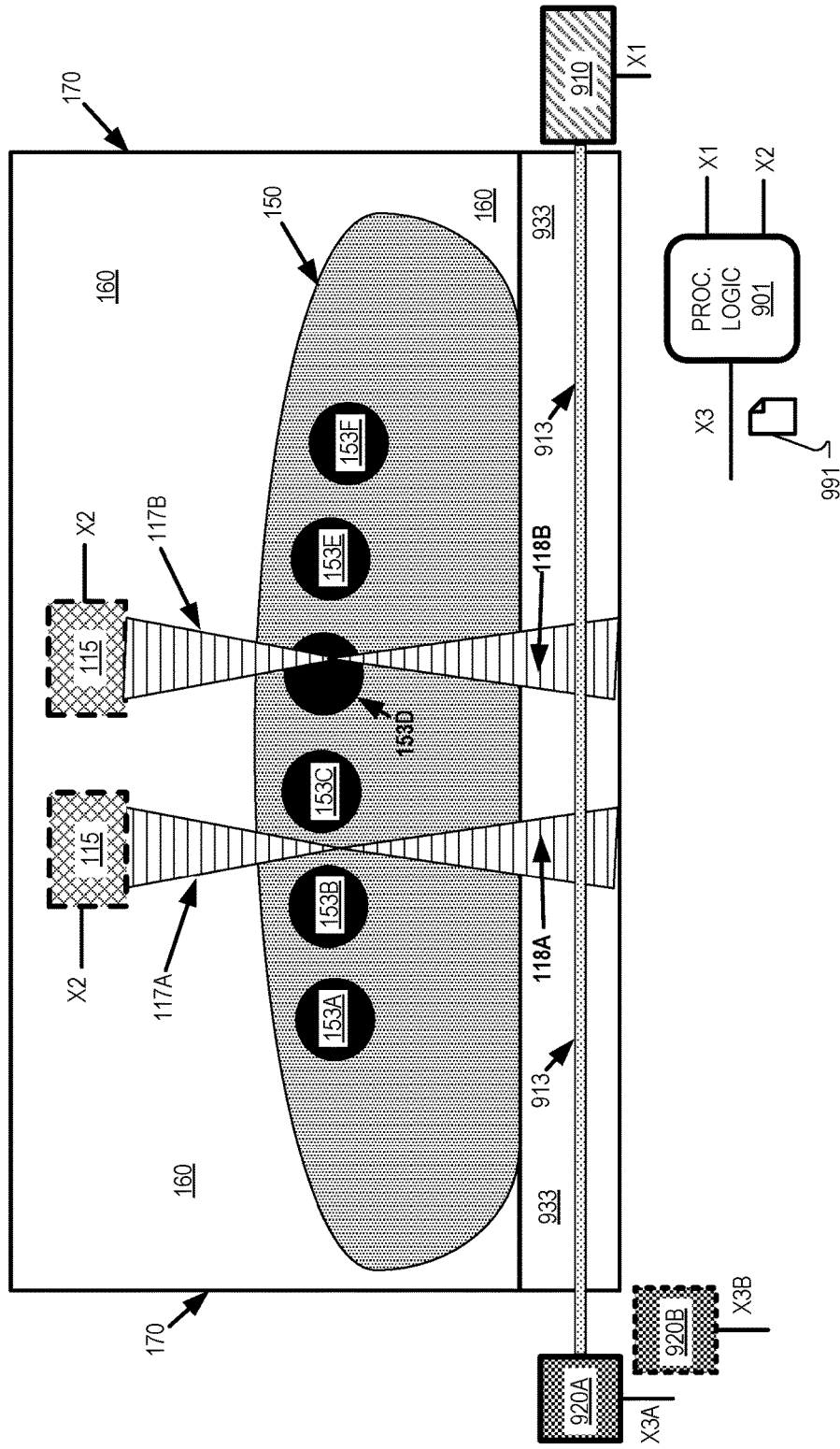
FIG. 9A illustrates an imaging system including a laser, a light detector, an ultrasound emitter, and an optically transmissive layer that is conducive to transmission of ultrasound signals, in accordance with aspects of the disclosure.

FIG. 9A illustrates an imaging system 900 including a light source 910, a light detector 920, an ultrasound emitter 115, and an optically transmissive layer 933 that is conducive to transmission of ultrasound signals, in accordance with aspects of the disclosure. Light source 910 is configured to emit a light beam 913 through optically transmissive layer 933. Light source 910 may be a laser light source emitting a laser light beam 913. Light detector 920A is configured to receive an exit signal of light beam 913 exiting optically transmissive layer 933. The exit signal may be a laser exit signal when light source 910 is a laser light source 910. Optically transmissive layer 933 is also configured to transmit ultrasound frequencies. Optically transmissive layer 933 may include glass or transparent plastic that contains an optically transmissive fluid or a gel to allow for transmission of ultrasound signals. Ultrasound emitter 115 is configured to emit an ultrasound signal 117 into sample 150 and light beam 913 propagating through optically transmissive layer 933 is positioned to receive an ultrasound exit signal 118 of the ultrasound signal exiting the sample 150.

Light detector 920 may include an image pixel array in a camera. The camera may be configured to capture an image of the exit signal of light beam 913 exiting the optically transmissive layer 933. Light detector 920 may include a photodiode or a plurality of photodiodes.

In operation, processing logic 901 may activate light source 910, by way of communication channel X1, to emit light beam 913 into optically transmissive layer 933. Processing logic 901 may drive ultrasound emitter 115, by way of communication channel X2, to emit an ultrasound signal 117 into sample 150. Processing logic 901 may then drive light detector 920A or light detector 920B to capture a signal 991 by way of communication channel X3.

Figure 9B:
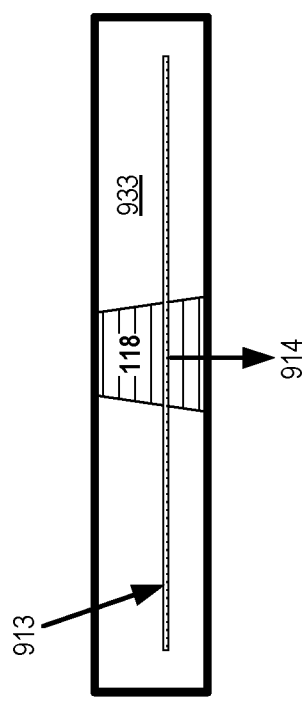
FIG. 9B illustrates a side view of an optically transmissive layer showing a laser light beam emitted in a two-dimensional plane, in accordance with aspects of the disclosure.

FIG. 9B illustrates a side view of optically transmissive layer 933 showing that the laser light beam 913 may be a two-dimensional plane configured to receive the ultrasound exit signal 118. Ultrasound exit signal 118 encounters light beam 913 as it exits sample 150 and diffracts a portion of light beam 913 as diffracted light 914. In some embodiments, multiple light beams similar to light beam 913 are emitted by multiple light sources similar to light source 910 and ultrasound exit signal 118 may also encounter and diffract the additional light beams.

Figure 9D:
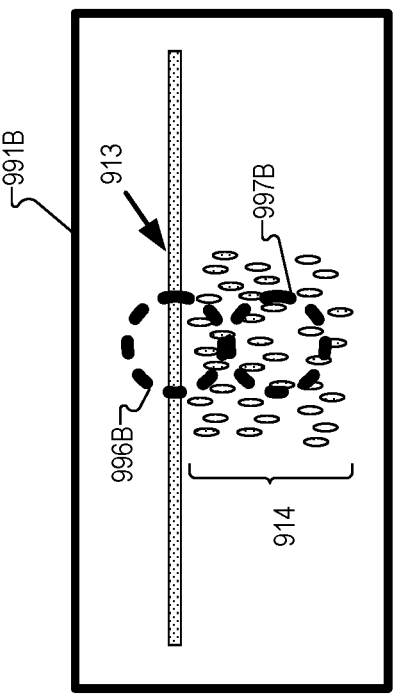
FIGS. 9C and 9D illustrate example images of laser light beams, in accordance with aspects of the disclosure.
Figure 9C:
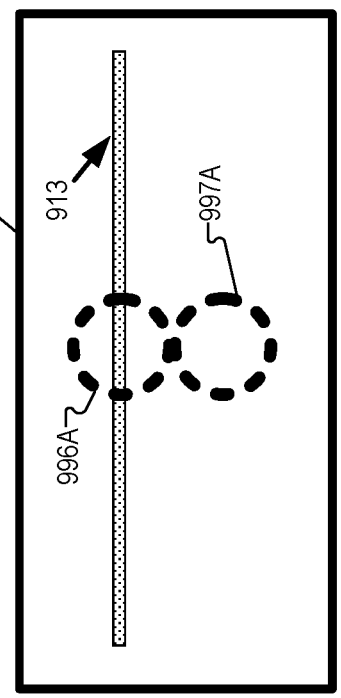

FIG. 9C illustrates an example image 991A generated by a camera of light detector 920A when ultrasound exit signal 118 is not diffracting light beam 913.

FIG. 9D illustrates an example image 991B generated by a camera of light detector 920A when light beam 913 is diffracted by ultrasound exit signal 118. When ultrasound signal 117 is focused to a voxel of sample 150 that has dense mechanical contrast (e.g. bone 153D), ultrasound exit signal 118B will be significantly attenuated and diffract less of light beam 913 so that diffracted light 914 is of a lower intensity.

By way of example, image region 996A of image 991A will have a very high intensity and region 997B will have very low intensity or no intensity when ultrasound exit signal 118 does not diffract light beam 913. Yet, when ultrasound exit signal 118 does diffract light beam 913 as diffracted light 914, region 997B will have increased intensity compared with region 996B. And, when ultrasound signal 117 is focused to a mechanically sparse voxel of sample 150 (as with ultrasound signal 117A), diffracted light 914 will have a higher intensity in region 997B than when ultrasound signal 117 is focused to a mechanically dense voxel of sample 150 (as with ultrasound signal 117B focused to bone 153D).

In some implementations, instead of a camera being used in light detector 920A, a photodiode simply generates an analog signal 991 where the photodiode is configured to generate the analog signal 991 in response to light beam 913. The more laser light diffracted from light beam 913, the smaller the analog signal 991 becomes. A plurality of photodiodes generating a plurality of analog signals may be used in some contexts.

In some implementations, a light detector 920B may configured to receive diffracted light 914 but not configured to receive undiffracted light beam 913. In this context, the lower the intensity of diffracted light 914 incident on light detector 920B, the weaker the ultrasound exit signal 118 and thus, the denser the voxel that ultrasound exit signal is focused to. Light detector 920B may be disposed in an offset position from light beam 913 such that light detector 920B only receives diffracted light 914 and does not receive undiffracted light beam 913. Light detector 920B may include an image pixel array or a photodiode to measure the intensity of diffracted light 914.

In an embodiment, processing logic 901 is configured to receive signal 991. Signal 991 may be an analog or digital signal or an image. A voxel value may be determined based on signal 991 and the voxel value may be incorporated into a composite image of sample 150. Determining the voxel value may include analyzing a diffraction pattern of an image. Determining the voxel value may include analyzing particular regions of the image for average light intensity.

In an embodiment, a diffraction value of laser light is measured. The diffraction value may be an intensity of diffracted laser light 914, for example. A first voxel value may be generated based on the diffraction value and the first voxel value may be incorporated into a composite image of the sample.

The disclosed imaging systems 100, 600, and 900 may benefit from having measurement beams 113, 613, and laser light beam 913 propagating outside the sample 150. This may improve imaging for live tissue where movement of the tissue in a sample is present. The disclosed imaging systems 100, 600, and 900 may be more sensitive than traditional ultrasound imaging techniques.

The term "processing logic" (e.g. processing logic 101, 501, 601, 801, or 901) in this disclosure may include one or more processors, microprocessors, multi-core processors, Application-specific integrated circuits (ASIC), and/or Field Programmable Gate Arrays (FPGAs) to execute operations disclosed herein. In some embodiments, memories (not illustrated) are integrated into the processing logic to store instructions to execute operations and/or store data. Processing logic may also include analog or digital circuitry to perform the operations in accordance with embodiments of the disclosure.

A "memory" or "memories" described in this disclosure may include one or more volatile or non-volatile memory architectures. The "memory" or "memories" may be removable and non-removable media implemented in any method or technology for storage of information such as computer-readable instructions, data structures, program modules, or other data. Example memory technologies may include RAM, ROM, EEPROM, flash memory, CD-ROM, digital versatile disks (DVD), high-definition multimedia/data storage disks, or other optical storage, magnetic cassettes, magnetic tape, magnetic disk storage or other magnetic storage devices, or any other non-transmission medium that can be used to store information for access by a computing device.

Communication channels may include or be routed through one or more wired or wireless communication utilizing IEEE 802.11 protocols, BlueTooth, SPI (Serial Peripheral Interface), I$^2$C (Inter-Integrated Circuit), USB (Universal Serial Port), CAN (Controller Area Network), cellular data protocols (e.g. 3G, 4G, LTE, 5G), optical communication networks, Internet Service Providers (ISPs), a peer-to-peer network, a Local Area Network (LAN), a Wide Area Network (WAN), a public network (e.g. "the Internet"), a private network, a satellite network, or otherwise.

A computing device may include a desktop computer, a laptop computer, a tablet, a phablet, a smartphone, a feature phone, a server computer, or otherwise. A server computer may be located remotely in a data center or be stored locally.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An imaging system comprising:
   a light scattering layer;
   a first laser configured to emit first laser light into the light scattering layer, wherein the light scattering layer is configured to scatter the first laser light;
   a first light detector configured to generate a first signal in response to a first measurement beam of the first laser light exiting the light scattering layer into the first light detector;
   an ultrasound emitter configured to emit an ultrasound signal into a sample;
   a second laser configured to emit second laser light into the sample; and
   a second light detector configured to generate a second signal in response to a second measurement beam of the second laser light exiting the sample, wherein the first measurement beam and the second measurement beam are positioned to be encountered by the ultrasound signal.

2. The imaging system of claim 1, wherein the first laser light is visible light, and wherein the second laser light is infrared light.

3. The imaging system of claim 2, wherein the first laser light is between 380 nm and 550 nm.

4. The imaging system of claim 1, wherein the first measurement beam is confined to the first scattering layer.

5. The imaging system of claim 1, wherein the first signal is generated by the first light detector during a same time period as the second signal is generated by the second light detector.

6. The imaging system of claim 1, wherein a first filter is disposed over the first light detector configured to pass the first laser light and reject the second laser light, and wherein a second filter is disposed over the second light detector configured to pass the second laser light and reject the first laser light.

7. The imaging system of claim 1, wherein the first measurement beam is formed between the first laser and the first light detector, and wherein the second measurement beam is formed between the second laser and the second light detector, the second measurement beam being positioned to receive an ultrasound exit signal of the ultrasound signal exiting the image sample, and wherein the first measurement beam is positioned to be encountered by the ultrasound signal within the sample.

8. A method of imaging a sample, the method comprising:
   generating a first signal with a first light detector in response to an ultrasound signal encountering a first measurement beam;
   generating a second signal with a second light detector in response to the ultrasound signal encountering a second measurement beam, wherein the second measurement beam propagates through the sample and the first measurement beam propagates outside the sample; and
   generating a composite image of the sample based on the first signal and the second signal.

9. The method of claim 8, wherein generating a composite image includes:
   generating a mechanical contrast value from the first signal;
   generating an optical contrast value, wherein generating the optical contrast value includes reducing a representation of the second signal by the mechanical contrast value; and incorporating the optical contrast value as a voxel value into the composite image of the sample, wherein the composite image is an optical contrast composite image.

10. The method of claim 9 further comprising:
incorporating the mechanical contrast value as a second voxel value into a mechanical contrast composite image of the sample.

11. The method of claim 8, wherein generating the first signal includes emitting first laser light from a first laser and the first measurement beam is the first laser light propagating between the first laser and the first light detector, and wherein generating the second signal includes emitting second laser light from a second laser having a second wavelength different from the a first wavelength of the first laser light, and wherein the second measurement beam is the second laser light propagating between the second laser and second light detector.

12. The method of claim 11, wherein the first laser light is emitted into a light scattering layer configured to scatter the first laser light, and wherein the first light detector is configured to receive the first measurement beam from the light scattering layer.

13. The method of claim 8 further comprising:
focusing a second ultrasound signal to a second voxel in the sample, wherein the ultrasound signal was focused on a first voxel of the sample and the second ultrasound signal is focused to the second voxel subsequent to the first ultrasound focused to the first voxel;
generating a third signal with the first light detector in response to the second ultrasound signal encountering the first measurement beam;
generating a fourth signal with the second light detector in response to the second ultrasound signal encountering the second measurement beam; and
augmenting the composite image of the sample based on the third signal and the fourth signal.

14. The method of claim 8, wherein the first measurement beam has a first wavelength of less than 600 nm or more than 1000 nm, and wherein the second measurement beam has a second wavelength between 600 nm and 1000 nm.

15. The method of claim 8, wherein at least a portion of the first measurement beam formed between the first laser and the first light detector is wavelength-shifted by the ultrasound signal subsequent to the ultrasound signal propagating through the sample.

16. The method of claim 8, wherein the ultrasound signal encounters the first measurement beam outside the sample, and wherein the ultrasound signal encounters the second measurement beam inside the sample.

17. A method of imaging a sample, the method comprising:
emitting first laser light from a first laser into a light scattering layer, wherein the light scattering layer is configured to scatter the first laser light, and wherein the first laser light is visible light;
emitting second laser light from a second laser into the sample, wherein the second laser light is infrared light;
focusing an ultrasound signal to a voxel in a sample;
generating a first signal with a first light detector in response to the ultrasound signal encountering a first measurement beam formed between the first laser light and the first light detector, wherein the ultrasound signal encounters the first measurement beam within the light scattering layer;
generating a second signal with a second light detector in response to the ultrasound signal encountering a second measurement beam formed between the second laser light and the second light detector, wherein the ultrasound signal encounters the first measurement beam within the sample;
determining a mechanical contrast value from the first signal; and
determining an optical contrast value, wherein generating the optical contrast value includes reducing a representation of the second signal by the mechanical contrast value.

* * * * *